United States Patent [19]

Meneghin et al.

[11] Patent Number: 4,486,599
[45] Date of Patent: Dec. 4, 1984

[54] PROCESS FOR PREPARING THE 2',4'-DIFLUORO-4-HYDROXY-(1,1'-DIPHENYL)-3-CARBOXYLIC ACID

[75] Inventors: Mariano Meneghin, Revine-Lago; Piero Piccinelli, Sasso Marconi; Claudio Giordano, Vicenza, all of Italy

[73] Assignee: Zambon S.p.A., Vicenza, Italy

[21] Appl. No.: 516,356

[22] Filed: Jul. 22, 1983

[30] Foreign Application Priority Data

Jul. 22, 1982 [IT] Italy ................. 22516 A/82

[51] Int. Cl.³ ............................................. C07C 63/00
[52] U.S. Cl. ................................................... 562/469
[58] Field of Search .......................... 562/469

[56] References Cited

U.S. PATENT DOCUMENTS

| 4,131,618 | 12/1978 | Weinstock | 562/469 |
| 4,216,340 | 8/1980 | Weinstock | 562/469 |
| 4,237,315 | 12/1980 | Dolling | 562/469 |

FOREIGN PATENT DOCUMENTS

| 842280 | 5/1970 | Canada | 562/469 |
| 862163 | 1/1971 | Canada | 562/469 |

*Primary Examiner*—Paul J. Killos
*Attorney, Agent, or Firm*—Stevens, Davis, Miller & Mosher

[57] ABSTRACT

Process for carboxylating 2',4'-difluoro-4-hydroxy-1,1'-diphenyl or a derivative thereof with an alkaline alkylcarbonate at atmospheric pressure to afford 2',4'-difluoro-4-hydroxy-(1,1'-diphenyl)-3-carboxylic acid.

4 Claims, No Drawings

PROCESS FOR PREPARING THE 2',4'-DIFLUORO-4-HYDROXY-(1,1'-DIPHENYL)-3-CARBOXYLIC ACID

This invention relates to a process for preparing 2',4'-difluoro-4-hydroxy-(1,1'-diphenyl)-3-carboxylic acid (known as Diflunisal) by carboxylation of 2',4'-difluoro-4-hydroxy-1,1-diphenyl or a derivative thereof, with an alkaline alkylcarbonate at atmpospheric pressure.

Diflunisal is endowed with antiinflammatory activity and has the following formula

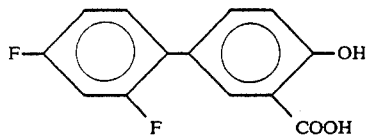
(I)

It may be prepared (Belgian Pat. No. 703,499) by carboxylation of the phenol of formula

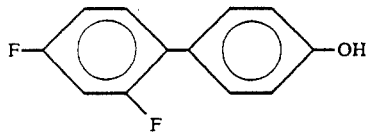
(II)

with carbon dioxide under pressure. U.S. Pat. No. 4,131,618 discloses a process for the preparation of Diflunisal by carboxylation of the acetyl-derivative of the phenol of formula II under pressure of carbon dioxide.

Both of these methods involve the use of special apparatus as horizontal autoclaves with scraping blades, whose cost is justified only if the compound is manufactured in big quantities. Another disadvantage of these processes is that by working in the presence of an excess of carbon dioxide it is not possible to avoid the formation of polycarboxylic derivatives.

Now it is been found that the carboxylation of the phenol of formula II may be carried out at atmospheric pressure in usual reactors at a very high conversion rate and in almost quantitative yield; i.e. by avoiding the formation of polycarboxylated by-products.

More particularly, the process of this invention is consisting in reacting the phenol of formula II with alkylcarbonates of alkaline metals in an atmosphere of an inert gas. Examples the alkaline alkylcarbonates which can be used according to this invention are: sodium ethylcarbonate, potassium ethylcarbonate, sodium methylcarbonate and potassium methylcarbonate which may be prepared according to usual techniques, by adding $CO_2$, in solid or gaseous form, to the corresponding alkaline alcoholate.

The phenol of formula II is directly added to the thus obtained suspension. Preferably at the ratio of one mole of the phenol to 1.5–2.5 mols of the alkylcarbonate.

After having removed the alcohol, the reaction mixture is heated at 150°–220° C.; before heating it may be added an inert diluent as for example vaseline oil in order to avoid the formation of masses.

The reaction is completed in 8–24 hours.

When the product submitted to carboxylation is a derivative of 2',4'-difluoro-4-hydroxy-1,1'-diphenyl such as, for example, its acetyl derivative, Diflunisal may be subsequently easily obtained according to known techniques.

The following examples are giving to illustrate the present invention, but in any case they are not limitative.

EXAMPLE

Preparation of 2',4'-difluoro-4-hydroxy-biphenyl-3-carboxylic acid with sodium methylcarbonate in a nitrogen atmosphere Into a solution of sodium methoxyde, obtained by dissolving metallic sodium (4.46 g; 0.19 mols) in methanol (100 ml), $CO_2$ is bubbled at 20° C. until the conversion of the methoxyde into the sodium methylcarbonate is completed.

2',4'-Difluoro-4-hydroxy-biphenyl (20 g; 0.097 mols) is added to the thus obtained suspension.

The solvent is distilled for recovering methanol (92 ml) up to an outer bath temperature of 120°–130° C.

The reaction mixture is placed in a nitrogen atmosphere and the outer bath temperature is increased gradually up to 200° C. and the mixture is maintained in these conditions for 8 hours.

The mixture is cooled and the raw product is dissolved in boiling water (800 ml).

After filtration and neutralization to pH 7 with concentrated HCl (10 ml) $K_2CO_3$ (10 g) is added. The thus obtained solution is extracted at 80° C. with 1,1,2-trichloro-ethylene (3×100 ml). From the combined organic extracts 2',4'-difluoro-4-hydroxy-biphenyl (1.6 g; 0.008 mols) is obtained by evaporation of the solvent at reduced pressure.

Into the aqueous solution, maintained at 80° C., is dropped a 15% hydrochloric acid solution (200 ml) under stirring.

The thus obtained suspension is extracted at room temperature with ethyl ether (300 ml). The organic layer is separated, dried and evaporated; a residue (21.8 g; 0.087 mols; yield, 98%) consisting of 2',4'-difluoro-4-hydroxy-biphenyl-3-carboxylic acid is thus obtained.

The same results have been obtained by working as above described but replacing the sodium methylcarbonate with the sodium ethylcarbonate.

We claim:

1. Process for preparing 2',4'-difluoro-4-hydroxy-(1,1'-diphenyl)-3-carboxylic acid which comprises the reaction of 2',4'-difluoro-4-hydroxy-1,1'-diphenyl or of a derivative thereof with an alkylcarbonate of an alkaline metal at atmospheric pressure.

2. Process according to claim 1, wherein 1.5–2.5 mols of an alkylcarbonate of an alkaline metal are used for each mole of 2',4'-difluoro-4-hydroxy-1,1'-diphenyl.

3. Process according to any of the preceding claims 1 and 2, wherein the reaction is carried out in an inert gas atmosphere.

4. Process according to claim 3, wherein the inert gas is nitrogen.